US006576258B1

(12) United States Patent
Kofler et al.

(10) Patent No.: US 6,576,258 B1
(45) Date of Patent: Jun. 10, 2003

(54) PHARMACEUTICAL FORMULATION WITH CONTROLLED RELEASE OF ACTIVE SUBSTANCES

(75) Inventors: Bojan Kofler, Škofja Loka (SI); Ljubomira Barbara Rebič, Ljubljana (SI); Judita Širca, Ljubljana (SI); Peter Venturini, Ljubljana (SI)

(73) Assignee: Lek, Tovarna Farmacevtskih In Kemicnih Izdelkov, D.D. (SI)

( * ) Notice: Subject to any disclaimer, the term of this patent is extended or adjusted under 35 U.S.C. 154(b) by 0 days.

(21) Appl. No.: 09/462,698

(22) PCT Filed: Jul. 13, 1998

(86) PCT No.: PCT/SI98/00014

§ 371 (c)(1),
(2), (4) Date: Jan. 12, 2000

(87) PCT Pub. No.: WO99/03453

PCT Pub. Date: Jan. 28, 1999

(30) Foreign Application Priority Data

Jul. 14, 1997 (SI) .................................. 9700186

(51) Int. Cl.$^7$ ............................ A61K 9/16; A61K 9/36; A61K 9/62; A61K 9/32; A61K 9/58
(52) U.S. Cl. ....................... 424/458; 424/457; 424/461; 424/468; 424/474; 424/490; 424/494; 424/462; 424/497; 424/480; 424/482; 514/772.3; 514/781; 514/785; 514/970
(58) Field of Search ................................ 424/451, 457, 424/458, 461, 462, 464, 465, 468, 470, 489, 490, 494, 495, 496, 497, 498, 480, 482

(56) References Cited

U.S. PATENT DOCUMENTS

| | | | |
|---|---|---|---|
| 2,540,979 A | | 2/1951 | Clymer et al. |
| 3,131,123 A | | 4/1964 | Masquelier |
| 4,478,819 A | | 10/1984 | Hercelin et al. |
| 4,738,974 A | | 4/1988 | Brändström |
| 4,786,505 A | * | 11/1988 | Lovgren et al. ............ 424/468 |
| 4,853,230 A | | 8/1989 | Lovgren et al. |
| 5,026,560 A | | 6/1991 | Makino et al. |
| 5,045,321 A | | 9/1991 | Makino et al. |
| 5,066,495 A | | 11/1991 | Moro et al. |
| 5,093,342 A | | 3/1992 | Tomoi et al. |
| 5,232,706 A | | 8/1993 | Palomo Coll |
| 5,246,714 A | | 9/1993 | Dahlinder et al. |
| 5,385,739 A | | 1/1995 | Debregeas et al. |
| 5,399,700 A | | 3/1995 | Min et al. |
| 5,433,959 A | * | 7/1995 | Makino et al. ............ 424/475 |
| 5,516,531 A | | 5/1996 | Makino et al. |
| 5,599,794 A | | 2/1997 | Eek et al. |
| 5,626,875 A | | 5/1997 | Ballester Rodes et al. |
| 5,629,305 A | | 5/1997 | Eek et al. |
| 5,997,903 A | | 12/1999 | Dietrich et al. |
| 6,013,281 A | | 1/2000 | Lundberg et al. |
| 6,077,541 A | | 6/2000 | Chen et al. |
| 6,096,340 A | | 8/2000 | Chen et al. |
| 6,149,942 A | | 11/2000 | Scheiwe et al. |

FOREIGN PATENT DOCUMENTS

| | | | |
|---|---|---|---|
| EP | | 005129 A1 | 10/1979 |
| EP | | 0 124495 | 11/1984 |
| EP | | 124495 A2 | 11/1984 |
| EP | | 077956 B1 | 7/1985 |
| EP | | 173664 A2 | 3/1986 |
| EP | | 0 237 200 | 9/1987 |
| EP | | 0 247 983 | 12/1987 |
| EP | | 519144 A1 | 12/1992 |
| EP | | 0 519 144 | 12/1992 |
| EP | | 0 519 365 | 12/1992 |
| GB | | 862376 | 3/1961 |
| GB | | 1485676 | 9/1977 |
| KR | | 92-8161 | 9/1992 |
| SE | WO | 96/24375 | * 8/1996 |
| WO | | 85/03436 | 8/1985 |
| WO | | 93/25204 | 12/1993 |
| WO | | 94/02140 | 2/1994 |
| WO | | 95/01783 | 1/1995 |
| WO | | 96/01622 | 1/1996 |
| WO | | 96/23500 | 8/1996 |
| WO | | 96/37195 | 11/1996 |
| WO | | 96/38175 | 12/1996 |
| WO | | 97/12581 | 4/1997 |

OTHER PUBLICATIONS

Amer. Pharm Assoc.; Pharm. Soc. of Great Britain: "Handbook of Pharmaceutical Excipients" 1986, American Pharmaceutical Assoc., Washington XP002086728 153140, pp. 135,139, 236.

Pilbrant et al., "Development of an oral formulation of omerprazole," Scand J. Gastroenterol, 20 (suppl 108) p. 113–120 (1985).

Unge et al., "Campylobacter pylori: Swedish experiences," Scand J. Gastroenterol Suppl. 157, p. 12–5 (1989).

* cited by examiner

Primary Examiner—James M. Spear
(74) Attorney, Agent, or Firm—Burns, Doane, Swecker & Mathis, LLP

(57) ABSTRACT

There is disclosed a method for stabilizing active substances that are unstable in acidic medium, unstable when stored for longer periods of time in the presence of water and at the same time sensitive to heating, by means of anhydrous granulation of active substances and dried pharmaceutically acceptable auxiliary substances for the preparation of pellet cores or granules. All pharmaceutically acceptable auxiliary substances employed are dried before use so that their weight loss at drying is less than 1.0% of the total weight of the pharmaceutically acceptable auxiliary substance, preferably less than 0.5%. Organic solvents used in process of anhydrous granulation should contain less than 0.2% of water. A novel pharmaceutical formulation with controlled release of active substances that are unstable in acidic medium, unstable when stored for longer periods of time in the presence of water and at the same time sensitive to heating, is disclosed as well.

52 Claims, No Drawings

PHARMACEUTICAL FORMULATION WITH CONTROLLED RELEASE OF ACTIVE SUBSTANCES

This application is a 371 of PCT/SI98/00014 filed Jul. 13, 1998.

TECHNICAL FIELD (A61K31/44,A61K 45/06,A61K 9/20,A61K 9/48)

The invention belongs to the field of pharmaceutical industry and relates to a novel medicinal formulation with controlled release of active substances on the basis of anhydrous (i.e. non-aqueous) granulation of the active substances and dried pharmaceutically acceptable auxiliary substances. By the invention a technologically simple manufacture of a stable pharmaceutical formulation with controlled release of active substances is made possible.

More specifically, the invention relates to a novel pharmaceutical formulation with controlled release of active substances that are unstable in acidic medium, unstable when stored for longer periods of time in the presence of water and at the same time sensitive to heating. Further, the invention relates to a novel method of stabilization of such unstable active substances and to a process for the preparation of the novel pharmaceutical formulation of such unstable active substances.

TECHNICAL PROBLEM

There exists a constant need for developing pharmaceutical formulations wherein in a technologically simple way there would be achieved a good stability of active substances that are unstable in acidic medium unstable when stored for longer periods of time in the presence of water and at the same time sensitive to hearing. For the manufacture of hitherto known pharmaceutical formulations containing such active substances, technological processes have been used, wherein also water, wherein such active substances are not stable, has been used as a solvent and therefore the required stability has been achieved especially by the addition of basic substances to the active substance or by using the active substance in the form of a salt thereof. Namely, basic substances create a basic pH in the environment of the active substance, whereat such active substances are more stable.

PRIOR ART

The first literature data upon stabilization of active substances that are unstable in acidic medium, unstable when stored for longer periods of time in the presence of water and at the same time sensitive to heating, relate to the transformation of such active substances to salts thereof, e.g. the transformation of omeprazol, which is a substance unstable in acidic medium, to different salts of omeprazol is disclosed in EP-A-124495. A pharmaceutical formulation with a magnesium salt of omeprazol is disclosed in WO 95/01783 and in WO 96/01622.

The use of basic inorganic salts of magnesium and/or calcium for stabilization of benzimidazoles is disclosed in EP-A-237200. A stable pharmaceutical formulation is prepared by a homogenous blending of the active substance with basic inorganic salts of magnesium and/or calcium and pharmaceutically acceptable auxiliary substances. The obtained granules, pellets or tablets are then coated with a gastro-resistant (i.e. enteric) coating.

The stabilization of omeprazol as disclosed in EP-A-247983 is achieved by means of a pharmaceutical formulation, wherein the active substance or a salt thereof is blended with different alkaline substances in the core and thereon one or more intermediate coatings (i.e. separating layers) are applied, followed by a gastro-resistant coating. In EP-A496437, which is a divisional of above EP-A-247983, a pharmaceutical composition comprising a benzimidazole active compound, a binder, a cellulose derivative, and a surfactant is disclosed. The stabilization of active substances that are unstable in acidic medium by adding different alkaline compounds is disclosed in several patent applications, e.g. in WO 94/02140 the addition of a coprecipitate $Al(QH)_3$-$NaHCO_3$ is disclosed, in U.S. Pat. No. 5,232,706 the addition of different alkaline compounds is disclosed and in EP-A-519365 there is disclosed a pharmaceutical formulation with pantoprazol, which is a substance unstable in acidic medium, and with alkaline compounds in the core. Additionally, the stability at prolonged storage is enhanced with the addition of $TiO_2$ to the core with omeprazol (WO 96/37195).

The formation of a complex of active substances unstable in an acidic medium, with cyclodextrins in an alkaline solution is disclosed in U.S. Pat. No. 5,399,700. The stabilization is achieved by incorporating a particular molecule of the active substance into a cyclodextrin molecule. Similarly, in WO 96/38175 the incorporating of molecules of benzimidazole derivatives into branched derivatives of cyclodextrin-carboxylic acid is disclosed.

In WO 93/25204 there is disclosed a stable pharmaceutical formulation of omeprazol microgranules containing a neutral core of sugar and starch, onto which core a layer of omeprazol and mannitol in equal quantities is applied. Similar pharmaceutical formulation for benzimidazole derivatives is also disclosed in WO 96/23500 and WO 97/12581. In a pharmaceutical formulation, disclosed in WO 97/12581, in an aqueous suspension a layer of omeprazol and hydroxypropylmethylcellulose is applied to inert cores of lactose. Other technologies of spraying an active substance onto inert cores are known as well (U.S. Pat. No. 5,246,714, EP-A-519144).

WO 96/24375 discloses a fixed formulation comprising an acid susceptible proton pump inhibitor and one or more antibacterial compounds. WO 83/03756 discloses the usage of anhydrous granulation to achieve rapid action of clometacine and to increase the biodisponibility of clometacine. EP-A-391374 relates to methods for the preparation of formulation of bromocriptine, which is very sensitive to moisture, light and temperature, by the incorporation of bromocriptine in an inert excipient.

THE INVENTIVE SOLUTION

The basic object of the invention is an improved stability of active substances that are unstable in acidic medium, unstable when stored for longer periods of time in the presence of water and at the same time sensitive to heating. This object is achieved by anhydrous granulation of the active substances and of dried pharmaceutically acceptable auxiliary substances for the preparation of pellet cores or granules. Pellet cores or granules thus prepared may under addition of dried pharmaceutically acceptable auxiliary substances be compressed into tablets, which are in the further procedure coated with a gastro-resistant coating. Between the tablet and the gastro-resistant coating one or more intermediate coatings may be optionally applied. Alternatively, the pellet cores or granules prepared by anhydrous granulation may be coated with a gastro-resistant coating and then filled into capsules, bags or compressed into tablets under the addition of dried pharmaceutically acceptable auxiliary substances. Between the pellet core or granules and a gastro-resistant coating one or more intermediate coatings may be optionally applied.

The object of the invention is a method for stabilizing active substances that are unstable in acidic medium, unstable when stored for longer periods of time in the presence of water and at the same time sensitive to heating, by means of anhydrous granulation of active substances and dried pharmaceutically acceptable auxliay substances for the preparation of pellet cores or granules.

In active substances that are unstable in the presence of water, stability at prolonged storage is a special problem. Hitherto known technological processes for the preparation of pharmaceutical formulations with controlled release of active substances are based upon the use of water or a mixture of water and organic solvents for the granulation of active substances and pharmaceutically acceptable auxiliary substances. During the process of drying the pellet cores or granules, water and other solvents are removed by heating. However, a complete removal of water from a pharmaceutical formulation is not possible according to hitherto known and disclosed processes. In active substances that are unstable when stored for longer periods of time in the presence of water and at the same time sensitive to heating, a prolonged heating when drying should be avoided, which makes the removal of water even more difficult. Thus it was the basic object of the invention to prepare such a pharmaceutical formulation that will contain less than 1% water, preferably less than 0.5% water, and to use such a technological process which will use anhydrous medium in all steps of the process for the preparation of the pharmaceutical formulation, which applies to the process of granulation of active substances and pharmaceutically acceptable auxiliary substances as well as to the process of tie optional application of an intermediate coating and to the process of the application of a gastroresistant coating. At the same time, all pharmaceutically acceptable auxiliary substances used are dried before use, so that their weight loss at drying (i.e. water content) is less than 1.0% of the total weight of the pharmaceutical auxiliary substance, preferably less than 0.5%.

The unstability of active substances in an acidic medium is especially problematic after a peroral application of active substances, which decompose in an acidic gastric medium even before the systemic absorption. Thus the pharmaceutical formulation with such active substance should be prepared in such a way that it inhibits the dissolving of the active substance in the acidic gastric medium, but allows the dissolving of the active substance in the small intestine. This is achieved in such a way that onto the core with the active substance a gastro-resistant coating is applied, which protects the active substance against the acidic gastric medium, but is dissolved in the small intestine and thus a dissolution and systemic absorption of the active substance from the small intestine is made possible. Due to the acidity of the pharmaceutically acceptable auxiliary substances forming the gastro-resistant coating, a direct application of such compounds onto the pellet core with the active substance is problematic for two reasons. Because of a direct contact between the active substance that is unstable in an acidic medium and the acidic pharmaceutically acceptable auxiliary substance in the gastro-resistant coating, this gastro-resistant coating may cause the decomposition of the active substance during the storage of the pharmaceutical formulation. Secondly, after the peroral application of a pharmaceutical formulation with such active substance, a diffusion of water into the pellet core may occur in the stomach, the active substance in the core being stabilized with an alkaline substance. Due to the alkaline medium thus formed in the pellet core, the gastro-resistant coating is dissolved already in the acidic gastric medium and the active substance is caused to decompose. Therefore hitherto known pharmaceutical formulations with controlled release of active substances that are unstable in an acidic medium have one or more intermediate coatings incorporated between the pellet core and the gastro-resistant coating, which coatings enhance the stability of the active substance during storage and after peroral application. Since the stabilization method of the novel pharmaceutical formulation according to the invention is not based upon stabilizing the active substance with alkaline substances, but upon stabilization via an anhydrous granulation of the active substances and dried pharmaceutically acceptable auxiliary substances, it is not necessary to use an intermediate coating between the pellet core and the gastro-resistant coating to provide the required stability of the active substance.

It has been surprisingly found that anhydrous granulation of active substances and dried pharmaceutically acceptable auxiliary substances in the preparation of pellet cores or granules substantially enhances the stability of active substances that are unstable in acidic medium, unstable when stored for longer periods of time in the presence of water and at the same time sensitive to heating, over Prior Art processes wherein water is used as a solvent. Organic solvents used in the process for the preparation of the novel pharmaceutical formulation with controlled release of active substances have lower boiling points than water and may be thus much easier removed from the pellet cores or granules. Because of the use of anhydrous granulation in the preparation of the novel pharmaceutical formulation according to the invention and due to an effective removal of solvents from the pharmaceutical formulation, no such medium is present which could transfer H30+ions between the pellet core with the active substance and the gastro-resistant coating. This is another reason that no intermediate coating to provide the required stability at prolonged storage is necessary. Since the present invention does not employ the manner of stabilizing active substances by adding alkaline substances, there is also no risk of the dissolution of the gastro-resistant coating after peroral application as described above.

Because of the use of a process of anhydrous granulation of active substances and dried pharmaceutically acceptable auxiliary substances in the preparation of pellet cores, granules or tablets, the cores thus prepared are porous. Therefore between the core and the gastro-resistant coating one or more intermediate coatings may be optionally applied in order to cover the irregularities on the core surface and to reduce the necessary amount of the gastro-resistant coating.

Further, the invention relates to a novel pharmaceutical formulation with controlled release of active substances that are unstable in acidic medium, unstable when stored for longer periods of time in the presence of water and at the same time sensitive to heating, and of a combination of such active substances with other active substances.

A novel pharmaceutical formulation with controlled release of active substances according to the invention consists of a core and a gastro-resistant coating and between the core and the gastro-resistant coating one or more intermediate coatings may be optionally applied. Pellet cores or granules or tablets represent the core of the novel pharmaceutical formulation according to the invention.

The core of the novel pharmaceutical formulation with controlled release of active substances according to the invention contains active substances, a binder soluble in organic solvents, a cellulose ether, a surfactant and other common pharmaceutically acceptable auxiliary substances used in the preparation of solid pharmaceutical formulations such as fillers, disintegrators, swelling agents, glidants. Pharmaceutically acceptable auxiliary substances used are dried before use, so that their weight loss after drying is less than 1.0%, preferably less than 0.5 % of the total weight of the individual pharmaceutical auxiliary substance.

The novel pharmaceutical formulation with controlled release of active substances according to the invention may contain different active substances in an amount in the range from 0.1 to 95.0 wt.%, preferably from 0.5 to 80.0 wt.% with regard to the total weight of the core of the novel pharmaceutical formulation according to the invention. As active substances in the novel pharmaceutical formulation with controlled release of the active substance there may be used different active substances acting as analgesics, anticonvulsants, antiparkinsonics, anaestetics, antibiotics, antimalarial agents, antihypertensives, antihistaminics, antipyretics, alpha-blockers, alpha-adrenergic agonists, bactericides, bronchial dilators, beta-adrenergic stimulants, beta-adrenergic blockers, enzymes, contraceptives, cardiovascular active substances, calcium channel inhibitors, proton pump inhibitors, diuretics, hypnotics, hormones, hyperglycemics, hypoglycemics, muscle relaxants and contractors, parasympatho-mimetics, sedatives, sympathomimetics, tranquillizers, antimigraine agents, vitamins and any combinations thereof.

The novel pharmaceutical formulation with controlled release of active substances is especially suitable for benzimidazole derivatives such as lansoprazol, timoprazol, omeprazol, pantoprazol, leminoprazol, pariprazol, E-3810, S-4216, which are well known proton pump inhibitors, for pharmaceutically acceptable salts thereof, their optically active isomers and optically active isomers of the salts thereof.

The binder soluble in organic solvents, which is incorporated into the core of the pharmaceutical formulation according to the invention, makes possible an anhydrous granulation of the active substances and dried pharmaceutically acceptable auxiliary substances and acts as a binder in the preparation of pellet cores or granules. The solubility of the binder in organic solvents is essential for the preparation of pellet cores or granules according to the process of anhydrous granulation of active substances and dried pharmaceutically acceptable auxiliary substances. As an example of a binder soluble in organic solvents, there can be used the polymer polyvinyl pyrrolidone with the K-value (the relative viscosity of a compound in an aqueous solution with respect to water) in the range from 10 to 95, preferably in the range from 24 to 32, having an average molecular weight in the range from 2000 g/mole to 1100000 g/mole, preferably in the range from 25000 g/mole to 50000 g/mole. The binder soluble in organic solvents is present in the core of the novel pharmaceutical formulation according to the invention in an amount from 1 to 30 wt.%, preferably from 2 to 15 wt.% with regard to the total core weight. The used binder soluble in organic solvents is dried before use so that its weight loss at drying is less than 1.0%, preferably less than 0.5%.

The cellulose ether in the core of the novel pharmaceutical formulation according to the invention acts as a binder and at the same time as a disintegrator. As the cellulose ether there can be used methyl cellulose, ethyl cellulose, hydroxyethyl cellulose, propyl cellulose, hydroxypropyl cellulose, lower-substituted hydroxypropyl cellulose, hydroxypropylmethyl cellulose, carboxymethyl cellulose, preferably lower-substituted hydroxypropyl cellulose having the content of hydroxypropoxy groups in the range of from 5 to 16%. The cellulose ether is present in the core of the novel pharmaceutical formulation according to the invention in an amount from 2 to 60 wt.%, preferably from 5 to 30 wt.% with regard to the total core weight. The cellulose ether used is dried before use so that its weight loss at drying is less than 1.0%, preferably less than 0.5%.

The surfactant added into the core improves the wettability of the dried pharmaceutically acceptable auxiliary substances in the preparation of the novel pharmaceutical formulation according to the invention. The surfactant also improves the wettability, solubility and dissolution rate of the active substances after peroral application of the novel pharmaceutical formulation according to the invention. As the surfactant there may be used ionic surfactants such as sodium lauryl sulfate, or non-ionic surfactants such as different types of poloxamers (copolymers of polyoxyethylene and polyoxypropylene), natural or synthetic lecitins as well as esters of sorbitan and fatty acids (such as Span® (Atlas Chemie)), esters of polyoxyethylenesorbitan and fatty acids (such as Polisorbates or Tween® (Atlas Chemie)), polyoxyethylated hydrogenated castor oils (such as Cremophor® (BASF)), polyoxyethylene stearates (such as Myrj® (Atlas Chemie)) or any combinations of the said surfactants. The surfactant is present in the core in an amount from 0.1 to 20.0 wt.%, preferably from 0.2 to 10.0 wt.% with regard to the total core weight. The surfactant used is dried before use so that its weight loss after drying is less than 1.0%, preferably less than 0.5%.

The core of the novel pharmaceutical formulation with controlled release of active substances also contains other dried pharmaceutically acceptable auxiliary substances. The novel pharmaceutical formulation with controlled release of active substances may contain one or more fillers such as lactose, saccharose, glucose, starch, microcrystalline cellulose, mannitol, sorbitol, calcium hydrogen phosphate, aluminum silicate, sodium chloride and others, one or more binders such as starch, gelatine, polyvinyl pyrrolidone, cross-linked polyvinyl pyrrolidone, sodium alginate, microcrystalline cellulose, carboxymethyl cellulose, lower substituted hydroxypropyl cellulose and others, one or more disintegrators such as starch, sodium cross-linked carboxymethyl cellulose, cross-linked polyvinyl pyrrolidone, sodium starch glycolate and others, one or more glidants such as polyethylene glycols of different molecular weights, magnesium stearate, calcium stearate, aluminium stearate, stearic acid, palmitic acid, cetanol, stearol, talc and others, one or more lubricants such as stearic acid, magnesium stearate, calcium stearate, aluminum stearate, siliconized talc and others. Pharmaceutically acceptable auxiliary substances used are dried before use so that their weight loss at drying is less than 1.0%, preferably less than 0.5 % with regard to the total weight of a particular pharmaceutical auxiliary substance.

The cores are coated with a gastro-resistant coating which prevents the release of the active substance in the acidic gastric medium and at the same time makes possible a controlled release of the active substance from the novel pharmaceutical form in the small intestine. The gastroresistant coating consists of cellulose derivatives such as cellulose acetophthalate, hydroxypropylmethyl cellulose phthalate, copolymers of metacrylic acid, shellac, ethyl cellulose, hydroxypropylmethyl cellulose acetate succinate. Besides said polymers the gastro-resistant coating may additionally contain one or more plasticizers such as polyethylene glycols of different molecular weights, triethyl citrate, dibutyl sebacate, tributyl citrate, cetyl alcohol, olive oil or castor oil, monoglycerides and other common pharmaceutically acceptable auxiliary substances which are used in the preparation of gastro-resistant coatings such as talc, Polysorbate 80, pigments and magnesium stearate. The amount of gastro-resistant coating applied is from 5 to 30 wt.% with regard to the total core weight. The used pharmaceutically acceptable auxiliary substances forming the gastro-resistant coating are dried before use so that their weight loss at drying is less than 1.0%, preferably less than 0.5% of the total weight of the individual pharmaceutical auxiliary substance.

Between the core and the gastro-resistant coating one or more intermediate coatings may be optionally applied in order to cover irregularities on the surface of the cores that are porous due to the anhydrous granulation of active substances and dried pharmaceutically acceptable auxiliary substances. The intermediate coating consists of cellulose ether polymers soluble in organic solvents, such as hydroxypropylmethyl cellulose, hydroxypropyl cellulose, methyl cellulose, sodium carboxymethyl cellulose, ethyl cellulose, polivinyl pyrrolidones, vinyl pyrrolidone/vinyl acetate copolymer, polymetacrylates. The amount of the applied optional intermediate coating is from 0 to 15 wt.% with regard to the total core weight. The used pharmaceutically acceptable auxiliary substances forming the intermediate coating are dried before use so that their weight loss at drying is less than 1.0%, preferably less than 0.5% of the total weight of the individual pharmaceutical auxiliary substance.

Another object of the invention is a process for the preparation of the novel pharmaceutical formulation with controlled release of active substances that are unstable in acidic medium, unstable when stored for longer periods of time in the presence of water and at the same time sensitive to heating.

The first step of the process for the preparation of the novel pharmaceutical formulation with controlled release of active substances is anhydrous granulation of an active substance and dried pharmaceutically acceptable auxiliary substances so that their weight loss at drying is less than 1.0%, preferably less than 0.5%. Organic solvents used in the process of anhydrous granulation should contain less than 0.2% of water. The process of anhydrous granulation is carried out in such a way that a dried surfactant is dissolved in an organic solvent at room temperature and the obtained solution is sprayed in a fluidized bed granulator onto a homogenous powdery mixture containing active substances, a dried binder soluble in organic solvents, a dried cellulose ether and other dried pharmaceutically acceptable auxiliary substances. The organic solvents used for that purpose are selected from the group of alcohols, ketones, esters, ethers, aliphatic hydrocarbons, halogenated hydrocarbons, cycloaliphatic, aromatic, heterocyclic solvents and mixtures thereof. The plastic mixture obtained in the process of anhydrous granulation is formed into granules or pellet cores by common pharmaceutical technological processes such as extruding and spheronizing methods. The pellet cores or granules so formed are dried in a fluidized bed or in a chamber dryer at the temperature of inlet air from 35 to 45° C. until the weight loss at drying is less than 1.0 %, preferably less than 0.5% of the total weight of the pellet cores or granules. Under the addition of dried pharmaceutically acceptable auxiliary substances, dry pellet cores or granules may be compressed into tablets, which in further procedure are coated with a gastro-resistant coating. In view of the porosity of the tablets, also one or more intermediate coatings may be applied between the tablet and the gastro-resistant coating. Alternatively, pellet cores or granules prepared by means of anhydrous granulation may be coated with gastro-resistant coating and then filled into capsules or bags or compressed into tablets under addition of dried pharmaceutically acceptable auxiliary substances. In view of the porosity of pellet cores or granules, also one or more intermediate coatings may be applied between the pellet core or granule and the gastro-resistant coating.

The gastro-resistant coating and the optional intermediate coating are prepared in such a way that dried polymers with the weight loss at drying of less than 1.0%, preferably less than 0.5%, are dissolved in organic solvents containing less than 0.2% water. As organic solvents ethanol, methanol, isopropanol, acetone, methylene chloride, carbon tetrachloride or a mixture thereof may be used. To the polymer solution thus formed also the remaining dried pharmaceutically acceptable auxiliary substances with the weight loss at drying of less than 1.0%, preferably less than 0.5%, such as plasticizers, antiadhesives, fillers, wetting agents, pigments are added. The solution or suspension thus formed is sprayed onto cores in a fluidized bed granulator.

After the completed process of coating with gastro-resistant coating and optionally with an intermediate coating, the pellets of the novel pharmaceutical formulation with controlled release of an active substance according to the invention are dried in a fluidized bed at the temperature of inlet air from 30 to 35° C. until the weight loss at drying is less than 1.0%, preferably less than 0.5% of the total weight of pellets of the novel pharmaceutical formulation.

By the method of stabilization of active substances on the principle of anhydrous granulation of active substances and dried pharmaceutically acceptable auxiliary substances in the preparation of the novel phamaceutical formulation according to the invention, the stability of active substances that are unstable in acidic medium, unstable when stored for longer periods of time in the presence of water and at the same time sensitive to heating, is essentially enhanced. The use of the process of anhydrous granulation makes possible the preparation of the novel pharmaceutical formulation according to the invention at lower temperatures and with shorter times of drying the granulate. In all steps of the process for the preparation of the novel pharmaceutical formulation according to the invention, all substances entering the process contain less than 1.0%, preferably less than 0.5% water. By the selection of solvents with a boiling point lower than the boiling point of water, the removal thereof under milder conditions and in a shorter time is made possible, which contributes to a better stability of active substances that are sensitive to heating. Because of the use of the process of anhydrous granulation, it is not necessary to apply an intermediate coating between the core with the active substance and the gastro-resistant coating in order to provide for the required stability of the active substance in the pharmaceutical formulation. Since a smaller number of auxiliary substances is present in the novel pharmaceutical formulation according to the invention, less strain is put on the organism.

The invention is illustrated by the following Examples, which in no way limit the scope thereof.

EXAMPLE 1

Pellet cores:
Composition for 1000 g of pellet cores:

| | |
|---|---|
| omeprazol | 100 g |
| lower-substituted hydroxypropyl cellulose (13 to 16% of hydroxypropoxy groups) | 150 g |
| microcrystalline cellulose | 150 g |
| mannitol | 478 g |
| sodium cross-linked carboxymethyl cellulose | 50 g |
| polyvinyl pyrrolidone K 25 | 70 g |
| polyoxyethylated hydrogenated castor oil | 2 g |

A series of 1000 g of pellet cores was prepared according to the following procedure: 2 g of polyoxyethylated hydrogenated castor oil (Cremophor® RH 40) at room temperature were dissolved in 300 g of absolute ethanol. The obtained solution (302 g) was sprayed at room temperature in a fluidized bed granulator in a process of anhydrous granulation onto a previously prepared homogenous mixture of powdery components 100 g of omeprazol, 150 g of dried lower-substituted hydroxypropyl cellulose (L-HPC LH-20) (weight loss at drying 0.3%), 150 g of dried microcrystalline cellulose weight loss at drying 0.4%), 478 g of dried mannitol (weight loss at drying 0.4%), 50 g of dried sodium cross-linked carboxymethyl cellulose (weight loss at drying 0.3%) and 70% of dried polyvinyl pyrrolidone K 25 (weight loss at drying 0.4%). The plastic mixture so prepared was extruded and then spheronized. The obtained pellet cores were dried in a fluidized bed or in a chamber dryer at the temperature of inlet air of from 35° C. to 45° C. until the weight loss at drying was less than 0.5% of the total weight of pellet cores. Thus 1000 g of pellet cores were obtained.

Dissolution test (release rate)

Apparatus: Apparatus 2 (USP 23), 100 rpm

Medium: phosphate buffer pH=6.8

Temperature: 37° C.

Quantitative analysis: UV spectrophotometry $\lambda_{det}=300$ nm)

TABLE 1

The percentage of released omeprazol upon dissolution time

| Dissolution time (min) | The percentage of released omeprazol |
|---|---|
| 10 | 81.8 |
| 20 | 93.0 |
| 30 | 96.5 |
| 40 | 97.6 |

It is evident from the above Table that omeprazol is released from the pellet cores according to the requirements for pharmaceutical formulations with controlled release of the active substance, which formulations must provide for a quick release of the active substance in the small intestine at pH value of 6.8.

EXAMPLE 2

Pellet cores:
Composition for 1000 g of pellet cores:

| | |
|---|---|
| omeprazol | 100 g |
| lower-substituted hydroxypropyl cellulose (13 to 16% of hydroxypropoxy groups) | 100 g |
| microcrystalline cellulose | 100 g |
| anhydrous lactose | 578 g |
| sodium cross-linked carboxymethyl cellulose | 50 g |
| polyvinyl pyrrolidone K 25 | 70 g |
| Polysorbate 80 | 2 g |

Pellet cores were prepared according to the same process as in Example 1 except that dried mannitol was replaced by dried anhydrous lactose (weight loss at drying 0.3%) and the surfactant polyoxyethylated hydrogenated castor oil (Cremophor® RH 40) was replaced by Polysorbate 80.

Dissolution test (release rate)

Apparatus: Apparatus 2 (USP 23), 100 rpm

Medium: phosphate buffer pH=6.8

Temperature: 37° C.

Quantitative analysis: UV spectrophotometry ($\lambda_{det}=300$ nm)

TABLE 2

Percentage of released omeprazol upon dissolution time

| Dissolution time (min) | The percentage of released omeprazol |
|---|---|
| 10 | 92.3 |
| 20 | 96.5 |
| 30 | 96.4 |
| 40 | 96.2 |

It is evident from the above Table that omeprazol is released from the pellet cores according to the requirements for pharmaceutical formulations with controlled release of the active substance, which formulations must provide for a quick release of the active substance in the small intestine at pH value of 6.8.

EXAMPLE 3

Pellet cores:
Composition for 1000 g of pellet cores:

| | |
|---|---|
| lansoprazol | 100 g |
| microcrystalline cellulose | 200 g |
| mannitol | 598 g |
| sodium starch glycolate | 50 g |
| polyvinyl pyrrolidone K 25 | 50 g |
| Polysorbate 80 | 2 g |

Pellet cores were prepared according to the same process as in Example 1 except that the active substance omeprazol was replaced by lansoprazol, the dried lower-substituted hydroxypropyl cellulose (L-HPC LH-20) was replaced by dried microcrystalline cellulose (weight loss at drying 0.3%), dried sodium cross-linked carboxymethyl cellulose was replaced by dried sodium starch glycolate (Primojel) (weight loss at drying 4%) and the surfactant polyoxyethylated hydrogenated castor oil (Cremophor® RH 40) was replaced by Polysorbate 80.

Dissolution test (release rate)

Apparatus: Apparatus 2 USP 23), 100 rpm

Medium: phosphate buffer pH=6.8

Temperature: 37° C.

Quantitative analysis: UV spectrophotometry ($\lambda_{det}=300$ nm)

TABLE 3

Percentage of released lansoprazol upon dissolution time

| Dissolution time (min) | The percentage of released lansoprazol |
|---|---|
| 10 | 90.1 |
| 20 | 94.0 |
| 30 | 95.1 |
| 40 | 95.4 |

It is evident from the above Table that lansoprazol is released from the pellet cores according to the requirements for pharmaceutical formulations with controlled release of the active substance, which formulations must provide for a quick release of the active substance in the small intestine at pH value of 6.8.

EXAMPLE 4

Pellet cores: Composition for 1000 g of pellet cores:

| | |
|---|---|
| omeprazol | 100 g |
| lower-substituted hydroxypropyl cellulose (13 to 16% of hydroxypropoxy groups) | 100 g |
| microcrystalline cellulose | 100 g |
| anhydrous lactose | 598 g |
| sodium cross-linked carboxymethyl cellulose | 50 g |
| polyvinyl pyrrolidone K 25 | 50 g |
| Polysorbate 80 | 2 g |

Pellet cores were prepared according to the same process as in Example 2 except that a part of dried polyvinyl pyrrolidone K 25 was replaced by anhydrous dried lactose (weight loss at drying 0.3%).
Dissolution test (release rate) Apparatus: Apparatus 2 (USP 23), 100 rpm Medium: phosphate buffer pH=6.8 Temperature: 37° C. Quantitative analysis: UV spectrophotometry $\lambda_{det}$=300 nm)

TABLE 4

The percentage of released omeprazol upon dissolution time

| Dissolution time (min) | The percentage of released omeprazol |
|---|---|
| 10 | 83.7 |
| 20 | 98.4 |
| 30 | 99.3 |
| 40 | 98.8 |

It is evident from the above Table that omeprazol is released from the pellet cores according to the requirements for pharmaceutical formulations with controlled release of the active substance, which formulations must provide for a quick release of the active substance in the small intestine at pH value of 6.8.

EXAMPLE 5

Pellet cores: Compositions for 1000 g of pellet cores:

| | |
|---|---|
| omeprazol | 100 g |
| lower-substituted hydroxypropyl cellulose (13 to 16% of hydroxypropoxy groups) | 100 g |
| microcrystalline cellulose | 100 g |
| anhydrous lactose | 568 g |
| sodium cross-linked carboxymethyl cellulose | 50 g |
| polyvinyl pyrrolidone K 25 | 50 g |
| polyethylene glycol 6000 | 30 g |
| Polysorbate 80 | 2 g |

Pellet cores were prepared according to the same process as in Example 4 except that into a homogenous powdery mixture of the active substance and dried auxiliary substances 30 g of dried polyethylene glycol 6000 (weight loss at drying 0.3%) were added.
Dissolution Test (release rate) Apparatus: Apparatus 2(USP 23), 100 rpm Medium: phosphate buffer pH=6.8 Temperature: 37° C. Quantitative analysis: UV spectrophotometry $\lambda_{det}$=300 nm)

TABLE 5

The percentage of released omeprazol upon dissolution time

| Dissolution time (min) | The percentage of released omeprazol |
|---|---|
| 10 | 74.9 |
| 20 | 87.8 |
| 30 | 92.4 |
| 40 | 93.6 |

It is evident from the above Table that omeprazol is released from the pellet cores according to the requirements for pharmaceutical formulations with controlled release of the active substance, which formulations must provide for a quick release of the active substance in the small intestine at pH value of 6.8.

EXAMPLE 6

Pellet cores: Composition for 1000 g of pellet cores:

| | |
|---|---|
| omeprazol | 100 g |
| lower-substituted hydroxypropyl cellulose (13 to 16% of hydroxypropoxy groups) | 100 g |
| microcrystalline cellulose | 100 g |
| mannitol | 598 g |
| sodium cross-linked carboxymethyl cellulose | 50 g |
| polyvinyl pyrrolidone K 25 | 50 g |
| Polysorbate 80 | 2 g |

A series of 1000 g of pellet cores was prepared according to the following procedure: 2 g of Polysorbate 80 at room temperature were dissolved in 300 g of absolute ethanol. The obtained solution (302 g) was sprayed at room temperature in a granulator in a process of anhydrous granulation onto a previously prepared homogenous mixture of powdery components 100 g of omeprazol, 100 g of dried lower-substituted hydroxyproyl cellulose (L-HPC LH-20) (weight loss at drying 0.3%), 100 g of dried microcrystalline cellulose (weight loss at drying 0.4%), 598 g of dried mannitol (weight loss at drying 0.5%), 50 g of dried sodium cross-linked carboxymethyl cellulose (weight loss at drying 0.3%) and 50 g of dried polyvinyl pyrrolidone K 25 (weight loss at drying 0.4%). The plastic mass so prepared was extruded and then spheronized. The obtained pellet cores were dried in a fluidized bed or in a chamber dryer at the temperature of inlet air of from 35° C. to 45° C. until the weight loss at drying was less than 0.5% of the total weight of the pellet cores. Thus 1000 g of pellet cores were obtained.

Dissolution test (release rate) Apparatus: apparatus 2 (USP 23), 100 rmp Medium: phosphate buffer pH=6.8 Temperature: 37° C. Quantitative analysis: UV spectrophotometry $\lambda_{det}$=300 nm)

TABLE 6

The percentage of released omeprazol upon dissolution time

| Dissolution time (min) | The percentage of released omeprazol |
|---|---|
| 10 | 83.5 |
| 20 | 93.2 |
| 30 | 95.6 |
| 40 | 96.7 |

It is evident from the above Table that omeprazol is released from the pellet cores according to the requirements for pharmaceutical formulations with controlled release of the active substance, which formulations must provide for a quick release of the active substance in the small intestine at pH value of 6.8.

EXAMPLE 7

Pellets—novel pharmaceutical formulation with controlled release of active substance Pellet cores with the same composition as in Example 6 were prepared in the same way as disclosed in Example 6. For the preparation of a gastro-resistant coating of 1000 g pellet cores the following dried auxiliary substances were necessary:

| pellet cores | 1000 g |
|---|---|
| hydroxypropylmethyl celllulose phthalate | 150 g |
| dibutyl sebacate | 5 g |

150 g of dried hydroxypropylmethyl cellulose phthalate (weight loss at drying 0.5%) and 5 g of dibutyl sebacate (at most 0.1% water) at room temperature were dissolved in a mixture of 1030 g of absolute ethanol (at most 0.2% water) and 1030 g of acetone (at most 0.2% water). The obtained solution was sprayed onto the pellet cores in the spraying device. The obtained coated pellets were filled into hydroxypropylmethyl cellulose capsules.
Dissolution test (release rate) Apparatus: Apparatus 2 (USP 23), 100 rpm Medium 1: 2 hours; artificial gastric juice pH 1.2 (500 ml) Medium 2: 30 min; phosphate buffer pH =6.8 (900 ml) Temperature: 37° C. Quantitative analysis: HPLC

TABLE 7

The percentage of non-dissolved and released omeprazol upon medium and dissolution time, resp.

| Dissolution time medium 1 | Percentage of non-dissolved omeprazol |
|---|---|
| 2 hours | 90.9 |

| Dissolution time medium 2 | Percentage of released omeprazol |
|---|---|
| 10 min | 79.0 |
| 20 min | 82.0 |
| 30 min | 88.6 |

It is evident from the above Table that omeprazol was released from the pellets according to the requirements for pharmaceutical formulations with controlled release of the active substance, which formulations should by means of a gastro-resistant coating prevent the release of the active substance in the acidic gastric medium (medium 1) and provide for a quick release of the active substance in the small intestine (medium 2).

EXAMPLE 8

Tablet—novel pharmaceutical formulation with controlled release of active substance Pellet cores with the same composition as in Example 6 were prepared in the same way as disclosed in Example 6. Pellets were prepared according to the same composition and procedure as disclosed in Example 7. The prepared coated pellets were used for the manufacture of tablets. Composition for one tablet:

| pellets | 231 mg |
|---|---|
| mannitol | 234 mg |
| polyethylene glycol | 25 mg |
| magnesium stearate | 10 mg |

To the obtained pellets dried mannitol (weight loss at drying 0.2%), dried polyethylene glycol (weight loss at drying 0.4%) and dried magnesium stearate (weight loss at drying 0.2%) were added and the obtained mixture was homogeneously blended. The mixture thus prepared was compressed into tablets in a common tablet compressing machine to obtain tablets having a weight of 500 mg.

Dissolution test (release rate) Apparatus: Apparatus 2 (USP 23), 100 rpm Medium 1: 2 hours; artificial gastricjuice pH 1.2 (500 ml) Medium 2: 30 min; phosphate buffer pH =6.8 (900 ml) Temperature: 37° C. Quantitative analysis: HPLC

TABLE 8

The percentage of non-dissolved and released omeprazol upon medium and dissolution time, resp.

| Dissolution time medium 1 | Percentage of non-dissolved omeprazol |
|---|---|
| 2 hours | 91.4 |

| Dissolution time medium 2 | Percentage of released omeprazol |
|---|---|
| 10 min | 80.4 |
| 20 min | 85.0 |
| 30 min | 90.1 |

It is evident from the above Table that omeprazol was released from the tablets according to the requirements for pharmaceutical formulations with controlled release of the active substance, which formulations should by means of a gastro-resistant coating prevent the release of the active substance in acidic gastric medium (medium 1) and provide for a quick release of the active substance in the small intestine (medium 2).

EXAMPLE 9

Pellets—novel pharmaceutical formulation with controlled release of active substance Pellet cores with the same composition as in Example 4 were prepared in the same way as disclosed in Example 4. For the preparation of a gastro-resistant coating of 1000 g of pellet cores the following dried auxiliary substances were necessary:

| | |
|---|---|
| pellet cores | 1000 g |
| hydroxypropylmethyl cellulose phthalate | 150 g |
| dibutyl sebacate | 15 g |

150 g of dried hydroxypropylmethyl cellulose phthalate (weight loss at drying 0.5%) and 15 g of dibutyl sebacate (at most 0.1% water) at room temperature were dissolved in a mixture of 1754 g of absolute ethanol and 438 g of acetone. The obtained solution was sprayed onto the pellet cores in a fluidized bed granulator. After the completed coating process, the pellets of the novel pharmaceutical formulation with controlled release were dried in a fluidized bed at the temperature of inlet air of from 30 to 35° C. until the weight loss at drying was less than 1.0%, preferably less than 0.5% of the total weight of the pellets. The obtained coated pellets were filled into capsules or bags or compressed into tablets under addition of dried pharmaceutically acceptable auxiliary substances.

Dissolution test (release rate) Apparatus: Apparatus 2 (USP 23), 100 rpm Medium 1: 2 hours; artificial gastric juice pH 1.2 (500 ml) Medium 2: 30 min; phosphate buffer pH =6.8 (900 ml) Temperature: 37° C. Quantitative analysis: HPLC

TABLE 9

The percentage of non-dissolved and released omeprazol upon medium and dissolution time, resp.

| Dissolution time medium 1 | Percentage of non-dissolved omeprazol |
|---|---|
| 2 hours | 95.9 |

| Dissolution time medium 2 | Percentage of released omeprazol |
|---|---|
| 10 min | 79.0 |
| 20 min | 92.0 |
| 30 min | 93.6 |

It is evident from the above Table that omeprazol was released from the pellets according to the requirements for pharmaceutical formulations with controlled release of the active substance, which formulations should by means of a gastro-resistant coating prevent the release of the active substance in acidic gastric medium (medium 1) and provide for a quick release of the active substance in the small intestine (medium 2).

EXAMPLE 10

Pellets—novel pharmaceutical formulation with controlled release of active substance Pellet cores with the same composition as in Example 4 were prepared in the same way as disclosed in Example 4. For the preparation of a gastro-resistant coating of 1000 g of pellet cores the following dried auxiliary substances were necessary:

| | |
|---|---|
| pellet cores | 1000 g |
| Eudragit | 150 g |
| dibutyl sebacate | 22 g |
| talc | 15 g |

150 g of dried Eudragit L 100 (weight loss at drying 0.3%) and 22 g of dibutyl sebacate were dissolved at room temperature in 1325 g of absolute ethanol and 15 g of talc were dispersed into the solution. The obtained suspension was sprayed onto the pellet cores under constant stirring in a fluidized bed granulator. After the completed coating process, the pellets of the novel pharmaceutical formulation with controlled release were dried in a fluidized bed at the temperature of inlet air of from 30 to 35° C. until the weight loss at drying was less than 1.0%, preferably less than 0.5% of the total weight of pellets. The obtained coated pellets were filled into capsules or bags or compressed into tablets under addition of dried pharmaceutically acceptable auxiliary substances.

Dissolution test (release rate) Apparatus: Apparatus 2 (USP 23), 100 rpm Medium 1: 2 hours; artificial gastric juice pH 1.2, 500 ml Medium 2: 30 min; phosphate buffer pH =6.8, 900 ml Temperature: 37° C. Quantitative analysis: HPLC

TABLE 10

The percentage of non-dissolved and released omeprazol upon medium and dissolution time, resp.

| Dissolution time medium 1 | Percentage of non-dissolved omeprazol |
|---|---|
| 2 hours | 95.1 |

| Dissolution time medium 2 | Percentage of released omeprazol |
|---|---|
| 10 min | 51.8 |
| 20 min | 88.3 |
| 30 min | 93.8 |

It is evident from the above Table that omeprazol was released from the pellets according to the requirements for pharmaceutical formulations with controlled release of the active substance, which formulations should by means of a gastro-resistant coating prevent the release of the active substance in acidic gastric medium (medium 1) and provide for a quick release of the active substance in the small intestine (medium 2).

EXAMPLE 11

Pellets—novel pharmaceutical formulation with controlled release of active substance Pellet cores with the same composition as in Example 4 were prepared in the same way as disclosed in Example 4. For the preparation of an intermediate coating and a gastro-resistant coating of 1000 g of pellet cores the following dried auxiliary substances were necessary:

| | |
|---|---|
| pellet cores | 1000 g |
| hydroxypropyl celllulose | 80 g |
| polyethylene glycol 6000 | 14 g |
| talc | 7 g |
| hydroxypropylmethyl cellulose phthalate | 165 g |
| dibutyl sebacate | 17 g |

80 g of dried hydroxypropyl cellulose (weight loss at drying 0.3%) and 14 g of dried polyethylene glycol 6000 (weight loss at drying 0.2%) were dissolved at room temperature in 1230 g of absolute ethanol, into the solution 7 g of talc were dispersed and the prepared dispersion was sprayed onto the pellet cores in a fluidized bed granulator. Onto the pellet cores coated with an intermediate coating, there was sprayed a gastro-resistant coating prepared in such a way that 165 g of dried hydroxypropylmethyl cellulose phthalate (weight loss at drying 0.4%) and 17 g dibutyl sebacate were dissolved in 1929 g of absolute ethanol and 482 g of acetone. After the completed coating process, the pellets of the novel pharmaceutical formulation with controlled release were dried in a fluidized bed at the temperature of inlet air of from 30 to 35° C. until the weight loss at drying was less than 1.0%, preferably less than 0.5% of the total weight of the pellets. The obtained coated pellets were filled into capsules or bags or compressed into tablets under addition of dried pharmaceutically acceptable auxiliary substances.

Dissolution test (release rate) Apparatus: Apparatus 2 (USP 23), 100 rpm Medium 1: 2 hours; artificial gastric juice pH 1.2, 500 ml Medium 2: 30 min; phosphate buffer pH=6.8, 900 ml Temperature: 37° C. Quantitative analysis: HPLC

TABLE 11

The percentage of non-dissolved and released omeprazol upon medium and dissolution time, resp.

| Dissolution time medium 1 | Percentage of non-dissolved omeprazol |
|---|---|
| 2 hours | 97.1 |

| Dissolution time medium 2 | Percentage of released omeprazol |
|---|---|
| 10 min | 88.4 |
| 20 min | 93.4 |
| 30 min | 96.7 |

It is evident from the above Table that omeprazol was released from the pellets according to the requirements for pharmaceutical formulations with controlled release of the active substance, which formulations should by means of a gastro-resistant coating prevent the release of the active substance in acidic gastric medium (medium 1) and provide for a quick release of the active substance in the small intestine (medium 2).

EXAMPLE 12

Pellets—novel pharmaceutical formulation with controlled release of active substance Pellet cores with the same composition as in Example 5 were prepared in the same way as disclosed in Example 5. For the preparation of an intermediate coating and a gastro-resistant coating of 1000 g of pellet cores the following dried auxiliary substances were necessary:

| pellet cores | 1000 g |
|---|---|
| hydroxypropyl celllulose | 80 g |
| polyethylene glycol 6000 | 14 g |
| talc | 7 g |
| Eudragit | 165 g |
| dibutyl sebacate | 25 g |
| talc | 17 g |

An intermediate coating was prepared and applied to the pellet cores in the same way as in Example 11. A gastro-resistant coating was prepared in such a way that 165 g of dried Eudragit L 100 (weight loss at drying 0.3%) were dissolved in 1457 g of absolute ethanol, into the obtained solution 25 g of dibutyl sebacate were added, 17 g of talc were dispersed and the obtained dispersion was sprayed in a fluidized bed granulator onto the pellet cores with an intermediate coating. After the completed coating process, the pellets of the novel pharmaceutical formulation with controlled release were dried in a fluidized bed at the temperature of inlet air of from 30 to 35° C. until the weight loss at drying was less than 1.0%, preferably less than 0.5% of the total weight of pellets. The obtained coated pellets were then dried and filled into capsules or bags or compressed into tablets under addition of dried pharmaceutically acceptable auxiliary substances.

Dissolution test (release rate) Apparatus: Apparatus 2 (USP 23), 100 rpm Medium 1: 2 hours; artificial gastric juice pH 1.2, 500 ml Medium 2: 30 min; phosphate buffer pH=6.8, 900 ml Temperature: 37° C. Quantitative analysis: HPLC

TABLE 12

The percentage of non-dissolved and released omeprazol upon medium and dissolution time, resp.

| Dissolution time medium 1 | Percentage of non-dissolved omeprazol |
|---|---|
| 2 hours | 96.1 |

| Dissolution time medium 2 | Percentage of released omeprazol |
|---|---|
| 10 min | 82.5 |
| 20 min | 91.2 |
| 30 min | 94.3 |

It is evident from the above Table that omeprazol was released from the pellets according to the requirements for pharmaceutical formulations with controlled release of the active substance, which formulations should by means of a gastro-resistant coating prevent the release of the active substance in acidic gastric medium (medium 1) and provide for a quick release of the active substance in the small intestine (medium 2).

EXAMPLE 13

Capsule—a combination of omeprazol with clarithromycin
Composition for one capsule:

| pellets | 250 mg |
|---|---|
| clarithromycin | 250 mg |

Pellets with the composition as disclosed in Example 9 were prepared in the same way as disclosed in Example 9. In an encapsulating machine 250 mg of pellets and 250 mg of clarithromycin per capsule were filled into capsules.

What is claimed is:

1. A method for stabilizing a therapeutically active substance comprising a benzimidazole derivative, comprising anhydrous granulation with an organic solvent of the active substance and dried pharmaceutically acceptable auxiliary substances for the preparation of pellet cores or granules, which are then either coated with a gastro-resistant coating or compressed into tablets under addition of a dried pharmaceutically acceptable auxiliary substance, which tablets are in further procedure coated with a gastro-resistant coating.

2. A method according to claim 1, characterized in that each pharmaceutically acceptable auxiliary substance employed is dried before use so that its weight loss at drying is in the range from 1.0% to 0.2% of the total weight of the pharmaceutical auxiliary substance.

3. A method according to claim 1, characterized in that each pharmaceutically acceptable auxiliary substance employed is dried before use so that its weight loss at drying is in the range from 0.5% to 0.2% of the total weight of the pharmaceutical auxiliary substance.

4. A method according to claim 1, characterized in that the organic solvent used in the process of anhydrous granulation, contains less than 0.2% of water.

5. Pharmaceutical formulation with controlled release of a therapeutically active substance comprising a benzimidazole derivative, characterized in that it consists of:
- an anhydrously-granulated core containing said therapeutically active substance, a binder soluble in an organic solvent, a cellulose ether, a surfactant, and one or more other pharmaceutically acceptable auxiliary substances; and
- gastro-resistant coating.

6. Pharmaceutical formulation according to claim 5, characterized in that the anhydrously-granulated core dried at a temperature of 35 to 45° C. has a water content such that the weight loss at drying is less than 1.0% of the total weight of the core.

7. Pharmaceutical formulation according to claim 6, characterized in that the anhydrously-granulated core dried at a temperature of 35 to 45° C. has a water content such that the weight loss at drying is less than 0.5% of the total weight of the core.

8. Pharmaceutical formulation according to claim 5, characterized in that the gastro-resistant-coated core dried at a temperature of 30 to 35° C. has a water content such that the weight loss at drying is less than 1.0% of the total weight of the formulation.

9. Pharmaceutical formulation according to claim 5, characterized in that said therapeutically active substance comprises a compound selected from the group consisting of omeprazol, an optically active isomer of omeprazol, a pharmaceutically acceptable salt of omeprazol, an optically active isomer of said salt, and combinations thereof.

10. Pharmaceutical formulation according to claim 5, characterized in that said therapeutically active substance comprises a compound selected from the group consisting of lansoprazol, an optically active isomer of lansoprazol, a pharmaceutically acceptable salt of lansoprazol, an optically active isomer of said salt, and combinations thereof.

11. Pharmaceutical formulation according to claim 5, characterized in that said therapeutically active substance comprises a compound selected from the group consisting of pantoprazol, an optically active isomer of pantoprazol, a pharmaceutically acceptable salt of pantoprazol, an optically active isomer of said salt, and combinations thereof.

12. Pharmaceutical formulation according to claim 5, characterized in that said therapeutically active substance is present in an amount of 0.1 to 95.0 wt.% with regard to the total weight of the core of the pharmaceutical formulation.

13. Pharmaceutical formulation according to claim 5, characterized in that the core of the pharmaceutical formulation contains a binder soluble in organic solvents with K value of 10 to 95.

14. Pharmaceutical formulation according to claim 5, characterized in that the core of the pharmaceutical formulation contains polyvinylpyrrolidone as a binder with an average molecular weight in the range from 2000 g/mole to 1100000 g/mole.

15. Pharmaceutical formulation according to claim 5, characterized in that the core of the pharmaceutical formulation contains polyvinylpyrrolidone as a binder in an amount of 1 to 30 wt.% with regard to the total weight of the core of the pharmaceutical formulation.

16. Pharmaceutical formulation according to claim 5, characterized in that the core of the pharmaceutical formulation contains a binder soluble in organic solvents, which is the polymer polyvinylpyrrolidone.

17. Pharmaceutical formulation according to claim 5, characterized in that the core of the pharmaceutical formulation contains a cellulose ether in an amount of 2 to 60 wt.% with regard to the total weight of the core of the pharmaceutical formulation.

18. Pharmaceutical formulation according to claim 5, characterized in that the core of the pharmaceutical formulation contains a cellulose ether selected from the group consisting of methyl cellulose, ethyl cellulose, hydroxyethyl cellulose, propyl cellulose, hydroxypropyl cellulose, lower-substituted hydroxypropyl cellulose, hydroxypropylmethyl cellulose, carboxymethyl cellulose, and combinations thereof.

19. Pharmaceutical formulation according to claim 5, characterized in that the core of the pharmaceutical formulation contains a cellulose ether, which is a lower-substituted hydroxypropyl cellulose having a content of hydroxypropoxy groups in the range of 5 to 16%.

20. Pharmaceutical formulation according to claim 5, characterized in that the core of the pharmaceutical formulation contains a surfactant in an amount of 0.1 to 20.0 wt.% with regard to the total weight of the core of the pharmaceutical formulation.

21. Pharmaceutical formulation according to claim 5, characterized in that the core of the pharmaceutical formulation contains a surfactant selected from the group consisting of sodium lauryl sulfate, poloxamers, natural and synthetic lecitins, esters of sorbitan and fatty acids, esters of polyoxyethylene sorbitan and fatty acids, polyoxyethylated hydrogenated castor oils, polyoxyethylene stearates and combinations thereof.

22. Pharmaceutical formulation according to claim 5, characterized in that the core of the pharmaceutical formulation contains one or more other pharmaceutically acceptable auxiliary substances selected from the group consisting of fillers, binders, disintegrators, glidants, lubricants, and combinations thereof.

23. Pharmaceutical formulation according to claim 5, characterized in that the gastro-resistant coating is present in an amount of 5 to 30 wt.% with regard to the total weight of the core of the pharmaceutical formulation.

24. Pharmaceutical formulation according to claim 5, characterized in that the gastro-resistant coating consists of one or more cellulose derivatives and one or more other pharmaceutically acceptable auxiliary substances.

25. Pharmaceutical formulation according to claim 24, characterized in that a cellulose derivative is selected from the group consisting of cellulose acetophthalate, hydroxypropylmethyl cellulose phthalate, and combinations thereof.

26. Pharmaceutical formulation according to claim 24, characterized in that one or more other pharmaceutically acceptable auxiliary substances is selected from the group consisting of polyethylene glycols, triethyl citrate, dibutyl sebacate, tributyl citrate, cetyl alcohol, olive oil, castor oil, monoglycerides, talc, Polysorbate 80, pigments, magnesium stearate, and combinations thereof.

27. Pharmaceutical formulation according to claim 5, characterized in that it is in the form of a capsule, bag, or tablet.

28. Process for the preparation of a pharmaceutical formulation with controlled release of a therapeutically active substance as set forth in claim 5, characterized in that
- a) a dried surfactant is in the process of anhydrous granulation dissolved in an organic solvent at room temperature and the obtained solution is sprayed in a fluidized bed granulator onto a homogenous powdery mixture of a therapeutically active substance, of dried binder soluble in organic solvents, of dried cellulose ether and of one or more other dried pharmaceutically acceptable auxiliary substances;

b) the obtained plastic mixture is formed into granules or pellet cores;

c) the obtained pellet cores or granules are dried in a fluidized bed or in a chamber drier at the temperature of inlet air of from 35 to 45° C. until the weight loss at drying is in the range from 1.0% to 0.2% of the total weight of pellet cores or granules;

d) the dry pellet cores or granules are under addition of one or more dried pharmaceutically acceptable auxiliary substances compressed into tablets, which are then coated with a gastro-resistant coating; or the dry pellet cores or granules are coated with a gastro-resistant coating and then filled into capsules, bags, or compressed into tablets under addition of one or more dried pharmaceutically acceptable auxiliary substances.

29. Process according to claim 28, characterized in that pellet cores or granules are dried in a fluidized bed or in a chamber drier at the temperature of inlet air of from 35 to 45° C. until the weight loss at drying is in the range from 0.5% to 0.2% of the total weight of pellet cores or granules.

30. Process according to claim 28, characterized in that after the completed process of coating with a gastro-resistant coating the pellets are dried in a fluidized bed at the temperature of inlet air of from 30 to 35° C. until the weight loss at drying is in the range from 1.0% to 0.2% of the total pellet weight.

31. Process according to claim 28, characterized in that after the completed process of coating with a gastro-resistant coating the pellets are dried in a fluidized bed at the temperature of inlet air from 30 to 35° C. until the weight loss at drying is in the range from 0.5% to 0.2% of the total pellet weight.

32. Process according to claim 28, characterized in that each pharmaceutically acceptable auxiliary substance employed is dried before use so that its weight loss at drying is in the range from 1.0% to 0.2% of the total weight of the pharmaceutical auxiliary substance.

33. Process according to claim 28, characterized in that each pharmaceutically acceptable auxiliary substance employed is dried before use so that its weight loss at drying is in the range from 0.5% to 0.2% of the total weight of the pharmaceutical auxiliary substance.

34. Process according to claim 28, characterized in that an organic solvent used in the process of anhydrous granulation contains less than 0.2% of water.

35. Process according to claim 28, characterized in that an organic solvent in the process of anhydrous granulation is selected from the group consisting of alcohols, ketones, esters, ethers, aliphatic hydrocarbons, halogenated hydrocarbons, cycloaliphatic solvents, aromatic solvents, heterocyclic solvents, and mixtures thereof.

36. A method according to claim 1, characterized in that said therapeutically active substance comprises a compound selected from the group consisting of rabeprazol, an optically active isomer of rabeprazol, a pharmaceutically acceptable salt of rabeprazol, an optically active isomer of said salt, and combinations thereof.

37. A method according to claim 36, characterized in that the active substance comprises rabeprazol.

38. Pharmaceutical formulation according to claim 5, characterized in that an active substance is selected from the group consisting of rabeprazol, an optically active isomer of rabeprazol, a pharmaceutically acceptable salt of rabeprazol, an optically active isomer of said salt, and combinations thereof.

39. Pharmaceutical formulation according to claim 5, characterized in that the anhydrously-granulated core has a water content such that the weight loss at drying is less than 1.0% of the total weight of the core.

40. Pharmaceutical formulation according to claim 39, characterized in that the anhydrously-granulated core has a water content such that the weight loss at drying is less than 0.5% of the total weight of the core.

41. Pharmaceutical formulation according to claim 8, characterized in that the gastro-resistant-coated core dried at a temperature of 30 to 35° C. has a water content such that the weight loss at drying is less than 0.5% of the total weight of the formulation.

42. A method according to claim 1, characterized in that the active substance comprises a compound selected from the group consisting of omeprazol, an optically active isomer of omeprazol, a pharmaceutically acceptable salt of omeprazol, an optically active isomer of said salt, and combinations thereof.

43. A method according to claim 1, characterized in that the active substance comprises a compound selected from the group consisting of lansoprazol, an optically active isomer of lansoprazol, a pharmaceutically acceptable salt of lansoprazol, an optically active isomer of said salt, and combinations thereof.

44. A method according to claim 1, characterized in that the active substance comprises a compound selected from the group consisting of pantoprazol, an optically active isomer of pantoprazol, a pharmaceutically acceptable salt of pantoprazol, an optically active isomer of said salt, and combinations thereof.

45. A method according to claim 42, characterized in that the active substance comprises omeprazol.

46. A method according to claim 43, characterized in that the active substance comprises lansoprazol.

47. A method according to claim 44, characterized in that the active substance comprises pantoprazol.

48. Pharmaceutical formulation according to claim 9, characterized in that said therapeutically active substance comprises omeprazol.

49. Pharmaceutical formulation according to claim 10, characterized in that said therapeutically active substance comprises lansoprazol.

50. Pharmaceutical formulation according to claim 11, characterized in that said therapeutically active substance comprises pantoprazol.

51. Pharmaceutical formulation according to claim 22, characterized in that said one or more other pharmaceutically acceptable auxiliary substances is selected from the group consisting of fillers consisting of lactose, saccharose, glucose, starch, microcrystalline cellulose, mannitol, sorbitol, calcium hydrogen phosphate, aluminum silicate, and sodium chloride;

binders consisting of starch, gelatine, polyvinylpyrrolidone, cross-linked polyvinylpyrrolidone, sodium alginate, microcrystalline cellulose, carboxymethyl cellulose, and lower-substituted hydroxypropyl cellulose;

disintegrators consisting of starch, sodium cross-linked carboxymethyl cellulose, cross-linked polyvinylpyrrolidone, and sodium starch glycolate;

glidants consisting of polyethylene glycols, magnesium stearate, calcium stearate, aluminum stearate, stearic acid, palmitic acid, cetanol, stearol, and talc;

lubricants consisting of stearic acid, magnesium stearate, calcium stearate, aluminum stearate, and siliconized talc; and combinations of the foregoing.

52. Pharmaceutical formulation according to claim 7, characterized in that said therapeutically active substance comprises rabeprazol.

* * * * *